(12) United States Patent
Shikinami et al.

(10) Patent No.: US 6,387,391 B1
(45) Date of Patent: May 14, 2002

(54) BIORESORBABLE POLYMERIC CLAYEY AND STICKY SUBSTANCE

(75) Inventors: Yasuo Shikinami; Hiroyuki Kawarada; Chika Nishi, all of Osaka (JP)

(73) Assignee: Takiron Co., Ltd., Osaka (JP)

( * ) Notice: Subject to any disclaimer, the term of this patent is extended or adjusted under 35 U.S.C. 154(b) by 0 days.

(21) Appl. No.: 09/292,744

(22) Filed: Apr. 16, 1999

(51) Int. Cl.[7] .............. A61K 31/74; A61K 31/715; A61K 33/00; A61K 35/12; A61K 38/00; A61K 45/00; A61K 47/00

(52) U.S. Cl. .............. 424/426; 424/78.08; 424/78.37; 424/78.38; 424/85.1; 424/94.1; 424/422; 424/423; 424/484; 424/486; 424/520; 424/548; 424/549; 424/600; 514/2; 514/54; 514/55; 514/57; 514/772.3; 514/772.7; 514/773; 514/774; 514/777; 514/781; 514/801; 514/802; 514/803; 523/105; 523/113; 523/115; 523/116; 528/403; 528/425

(58) Field of Search ............... 424/484, 485, 424/486, 487, 488, 77, 78.01, 78.02, 78.06, 78.07, 78.08, 78.37, 78.38, 94.1, 549, 422, 423, 426, 520, 548, 600, 602, 85.1; 514/2, 454, 55, 57, 772.3, 772.7, 773, 774, 777, 781, 801, 802, 803; 523/105, 113, 115, 116; 528/403, 425

(56) References Cited

U.S. PATENT DOCUMENTS

| 4,291,013 | A | * | 9/1981 | Wahlig et al. ............ 424/16 |
|---|---|---|---|---|
| 4,595,713 | A | | 6/1986 | Bennett et al. ............ 523/105 |
| 4,772,419 | A | * | 9/1988 | Mälson et al. ............ 252/315.1 |
| 5,143,730 | A | | 9/1992 | Fues et al. ............ 424/426 |
| 5,147,403 | A | * | 9/1992 | Gitelis ............ 623/16 |
| 5,201,733 | A | * | 4/1993 | Etheredge, III ............ 606/53 |
| 5,397,816 | A | * | 3/1995 | Reilly et al. ............ 523/113 |
| 5,649,959 | A | * | 7/1997 | Hannam et al. ............ 606/213 |

FOREIGN PATENT DOCUMENTS

| EP | 0 488 218 A | | 6/1992 |
|---|---|---|---|
| EP | WO 92 15340 A | | 9/1992 |
| EP | 0 594 148 | * | 4/1994 |
| EP | WO 9603159 A | | 2/1996 |
| EP | 0 714 666 A | | 6/1996 |
| EP | 0 722 966 A | | 7/1996 |
| EP | 0 747 072 A2 | | 12/1996 |

OTHER PUBLICATIONS

P.W. Atkins, "Physikalische Chemie", VCH10, Verlagsgesellschaft, Weinheim, Bundesrepublik Deutschland XP002125051, p. 159, Paragraph 2, 1$^{st}$ Edition (1987); 2$^{nd}$ Edition (1996).

* cited by examiner

Primary Examiner—Jose'G. Dees
Assistant Examiner—Frank Choi
(74) Attorney, Agent, or Firm—Sughrue Mion, PPLC

(57) ABSTRACT

This invention provides a claycy and sticky substance as a new biomaterial that cannot be found in the current medical field, which is bioresorbable, shows tackiness, plasticity and shape holding ability at a temperature of approximately from 30 to 40° C. and can give unrestricted shapes at body temperature or more by increasing its fluidity. This clayey and sticky substance comprises a copolymer of two or more bioresorbable monomers, preferably any one of copolymers of p-dioxanone with D-lactic acid, L-lactic acid, D,L-lactic acid, trimethylene carbonate and ε-caprolactone, or a mixture of two or more of these copolymers. This clayey and sticky or clayey substance is suited for a hemostatic material, an adhesive material for tissues, a prosthetic material for tissue reconstruction use, a carrier of drug delivery system, a plugging material, an accretion-preventing material and a scaffold material for tissue engineering use.

12 Claims, 1 Drawing Sheet

BIORESORBABLE POLYMERIC CLAYEY AND STICKY SUBSTANCE

FIELD OF THE INVENTION

This invention relates to a novel biomaterial which does not exist in the present medical field, namely a biodegradable polymeric clayey and sticky substance which has such properties that it shows tackiness, plasticity and shape holding ability at a temperature of from skin temperature to body temperature in human (approximately from 30 to 40° C.) and can give optional shapes at body temperature or more by increasing its fluidity, and to materials which use this novel polymeric clayey and sticky, such as a hemostatic material, an adhesive material for tissues, a prosthetic material for tissue reconstruction use, a carrier of drug delivery system (DDS), a plugging material, an accretion-preventing in material and a scaffold material for tissue engineering.

BACKGROUND OF THE INVENTION

Bioresorbable materials have been studied markedly actively in recent years and put into practical or trial use not only as sutures for surgical operation use but also as various osteosynthetic materials, carriers for the drug delivery system and scaffolds, fillers and prostheses for living body reconstruction in the tissue engineering.

Typical examples of polymers to be used for these many purposes include a wide variety of substances for various uses, such as polyglycolic acid (PGA), polylactic acid (PLA), PLA/PGA copolymer, polydioxanone (PDS), poly-ε-caprolactone (PCL), polytrimethylene carbonate (PTMC), poly-D,L-lactide (P-D,LLA) and other copolymers produced by using monomers which constitute these polymers.

As such polymers, substances having various molecular weights, ranging from a low molecular weight of several hundreds to a high molecular weight of exceeding one million, have been synthesized and examined for their suitability for respective uses. For example, amorphous polymers having low molecular weight have been tried for certain uses which do not require strength, such as carriers of DDS and scaffolds of living body reconstruction, and crystalline polymers having relatively large molecular weight have been put into practical use as sutures and osteosynthetic materials which require strength.

These materials, however, are limited to certain shapes such as fine powders, granules, films, sheets, porous bodies, fibers, filaments (threads), rods, plates and screws. These shapes can be changed only to such a degree that each material can be used by cutting it into a certain shape suited for its use, so that these materials cannot be used by changing them into desired shapes just before their use by optionally forming them into three-dimensional directions.

However, certain materials which are implanted into the living body in the action of surgical operation, such as hemostatic materials, adhesives, plugging materials, accretion-preventing materials, prosthetic and scaffold materials for use in the living body reconstruction and carriers of DDS, are ideal as biomaterials from the handling and functional points of view, with the proviso that each of them can be used by changing it easily into an optional shape fitted to the operating region when surgical operation is carried out and that, during the process of the resorption (i.e., degradation and absorption) of the material in the living body and its final excretion from the living body, tissues can gradually penetrate into a region where the material is indwelt and replace the region so that the shape and tissues can be reconstructed and restored into the original conditions. Unfortunately, however, virtually nothing is known so far about biomaterials which satisfy such requirements.

The following describes each of known cases.

[Hemostatic materials]

Among known hemostatic materials, bone wax conventionally used as a hemostatic material for stopping bleeding from the bone marrow is a product obtained using a natural material, bees wax, as the main component and mixing it with isopropyl palmitate and salicylic acid. This hemostatic material is frequently used in certain fields such as orthopedic surgery and plastic surgery where treatment of bones is carried out.

However, since this has poor biocompatibility and affinity and is not biodegradable, it remains as a foreign substance in the living body for a prolonged period of time and migrates inside the living body in some cases, so that this material may be excreted through the skin when used in a superficial disease close to the skin or it may induce infection or inflammation due to foreign body reactions in the living body.

[Adhesive materials]

The adhesive materials for medical use are divided into those which adhere (A) soft tissues and those which adhere (B) hard tissues (such as bones and teeth).

The materials (A) which adhere soft tissues include 1) cyanoacrylate system, (2) fibrin paste, (3) gelatin paste and (4) polyurethane system. However, the material (1) stimulates the living body when hardened and poses a problem in terms of the metabolism of degraded products. Also, the material (2) has low adhesive strength and has an immunological problem, and the material (3) also has low adhesive strength and toxicity of its cross-linking agent, formaldehyde or glutaraldehyde, causes a problem. In the case of the material (4), isocyanate as its starting material poses a problem in terms of its safety upon the living body.

On the other hand, among the materials (B) which adhere hard tissues (such as bones and teeth), bone cement is frequently used in which polymethyl methacrylate (PMMA) monomer (MMA) is mixed with powder of bioactive ceramics such as hydroxyapatite and peripheral hard tissues are adhered and repaired at the time of the polymerization curing of the mixture. This material, however, has disadvantages in that it generates considerably high temperature at the time of polymerization and damages the peripheral tissues by the heat, the monomer remained after the polymerization causes damage upon the living body due to its toxicity, and the poor toughness of the cement causes prolonged cement fracture or its delamination from the tissues.

The fibrin paste which is regarded as most useful material among the adhesive materials for use in soft tissues is a biomaterial originated from the living body and artificially uses the tissue conglutination reaction of fibrin. That is, this is a living body system adhesive material which uses its wound-conglutinating reaction in which a water-soluble plasma protein, fibrinogen, is selectively hydrolyzed into fibrin by the enzymatic action of thrombin and the conglutination is effected by the gelling of fibrin through its molecular association.

It has been tried to use this material as a substitute of sutures for the purpose of carrying out anastomosis of peripheral nerves and capillary vessels or in the field of blood vessel surgery and cranial nerve surgery for the purpose of reinforcing the operating area. It has been tried also in plastic surgery for the purpose of carrying out bone connection and in blood stanching and skin graft fixation of burn patients.

This fibrin paste has many advantages, for example, 1) it is a physiological function-applied adhesive material, 2) it is not related to platelets and in coagulopathy, 3) its adhesion is relatively quick, 4) it does not require excess heat and pressure, 5) it is not affected by moisture in the adhesion region and 6) it is appropriately absorbed due to it high affinity for tissues, but it also has fatal drawbacks in that its adhesion is weak and, being a blood preparation, it has a probability of causing viral infection. In addition, though it is known that this material has actions to enhance regeneration of capillary vessels and accelerate ossification, it has been used broadly but only as a hemostatic material.

Application of the adhesion by hardening of gelatin (collagen) to regions where not so strong adhesion is required has also been expected but hardly put into practical use in reality because of the toxicity of its hardening agent, foreign body reaction of the hardened gelatin and its insufficient physical characteristics.

[Reconstruction protecting materials, plugging materials, accretion-preventing materials, prosthetic materials, fillers, scaffolds for reconstruction use and carriers for drug delivery use]

Since it is desirable that these biomaterials are present temporarily in the living body for a temporal assistance of therapeutic treatments and then finally absorbed and excreted from the living body, it is desirable that raw materials which constitute these materials are bioresorbable as a general rule.

As an example of the reconstruction protecting materials, membranes for use in the treatment of periodontal diseases and reconnection of peripheral nerves have been examined. The object of these membranes is to secure places where tissues are regenerated, while positively assisting repair and reconstruction of tissues by keeping routes for supplying nutrients and cytokines as drugs into the tissues. Examples of the protecting membranes for reconstruction use include a non-absorbable micro-porous teflon (Goatics (registered trademark)) and absorbable materials such as poly-L-lactic acid, a copolymer of L-lactic acid with glycolic acid and a copolymer of L-lactic acid with e-caprolactone.

Similar porous and non-porous films or sheets have also been examined as accretion-preventing membranes.

Examples of the fillers so far examined include a membrane of low molecular weight poly-L-lactic acid, poly-D, L-lactic acid, a copolymer of D,L-lactic acid with ε-caprolactone or a copolymer of glycolic acid with ε-caprolactone, alone, or its powder or heteromorphic form, or powder or granules of hydroxyapatite or α- or β-tricalcium phosphate or its mixtures with the just described polymers.

As the carriers for use in the drug delivery system, certain materials such as non-porous or porous films, sheets (plates) and granules (powders) of the aforementioned copolymers have been examined.

Since the parts to be adhered are living bodies as has been described in the foregoing, the medical adhesive materials to be used in the living body require difficult conditions other than those for industrial purposes (particularly a condition that they are safe upon the living body), and it is not so easy to satisfy these conditions. Among clinical application cases of the aforementioned fibrin paste, there is a case which does not essentially require high adhesive strength. That is, it is used for the purpose of effecting temporal fixing so that spontaneous connection is completed thereafter by self-repair. In order to effect self-repair of damaged tissues, the adhesive material should not inhibit contact between newly formed tissues by remaining on the region to be adhered and connected. Also, this adhesive material must be a biocompatible material having no toxicity and injurious property as a matter of course. In addition, it is necessary that this material can be sterilized by a certain method.

The materials to be used as plugging materials, accretion-preventing materials, prosthetic materials or fillers will become more ideal biomaterials when they can simultaneously give a shape-reproducing function to restore the original shape of the damaged region and a positive chance for its treatment, in addition to their function to exist in the repairing and reconstructing region of the living body merely as a temporal plugging having a certain shape. That is, they will become more ideal biomaterials if they can be formed into the three-dimensional shape of the region of living body to be repaired, at will at the time of surgical operation, so that they can adhere to the peripheral tissues at the surface, and also if they can restore the living body both morphologically and functionally, by effecting transfer, induction and penetration of the peripheral tissues into the region during the process of their gradual degradable and absorption in the living body and their final excretion from the living body.

However, no biomaterial has been developed which has necessary characteristics for satisfying the just described object, namely (1) its fluidization and plastic deformation can be effected at a temperature not so higher than the body temperature so that it can be easily handled by surgions, (2) it shows tackiness with a living body heat, (3) it can be formulated and mixed intraoperatively without denaturing bio-substances or drugs such as bone fragments and hormones by heating high temperature and (4) the material is bioresorbable by itself and disappears at the relatively early stage after the treatment.

SUMMARY OF THE INVENTION

With the aim of creating a material having the aforementioned properties and providing it to the practical field, the inventors of the present invention have conducted intensive studies and achieved this object by not using a biomaterial having a probability of causing antigen-antibody reaction but by preparing and synthesizing a hydrolyzing type synthetic degradable and bioabsorbable polymer which undergoes enzyme-non-specific biodegradation.

That is, the bioresorbable clayey and sticky substance of the present invention which resolves the aforementioned problems is a copolymer comprising two or more bioresorbable monomers, wherein they show tackiness, plasticity and shape holding ability at a temperature of from skin temperature to body temperature in human (approximately from 30 to 40° C.) and can give optional shapes at a temperature which is higher than the body temperature but not so high temperature by further increasing its fluidity.

Other objects and advantages of the present invention will be made apparent as the description progresses.

DETAILED DESCRIPTION OF THE INVENTION

Figure 1:
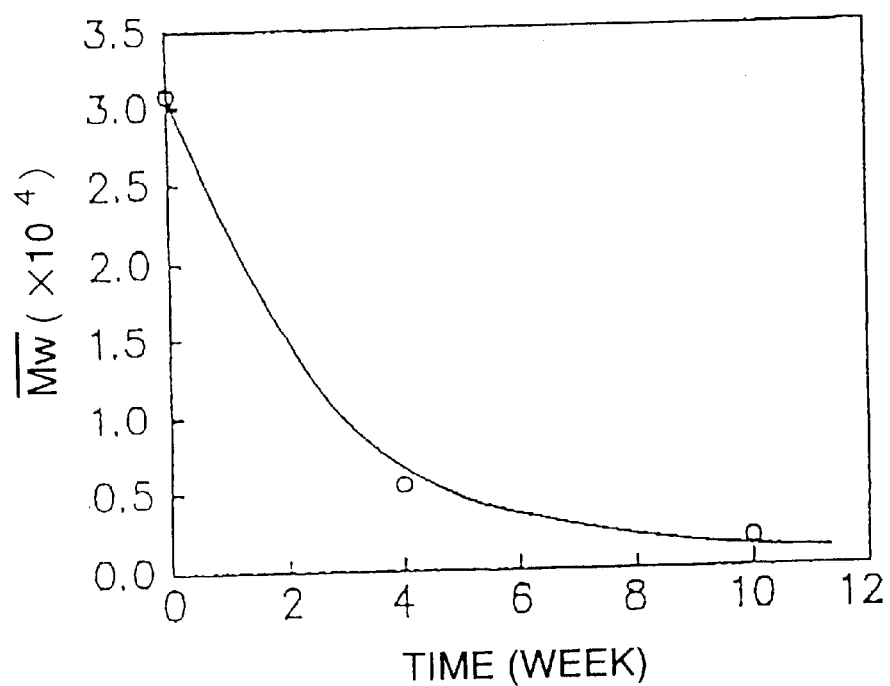
FIG. 1 is a graph showing periodical changes in the weight average molecular weight by hydrolysis when a in p-DOX/D,L-lactide copolymer according to an example of the present invention is soaked in phosphate buffer solution (PBS) at 37° C.

Illustrative examples of the bioresorbable polymeric clayey and sticky substance of the present invention include a clayey and sticky substance which is a copolymer of p-dioxanone with another bioresorbable monomer and has a weight average molecular weight of from 2,000 to 100,000, preferably a biodegradable polymeric clayey and sticky substance which comprises any one of a copolymer of p-dioxanone with D-lactide having a weight average molecular weight of from 2,000 to 40,000, a copolymer of p-dioxanone with L-lactide having a weight average molecular weight of from 2,000 to 40,000, a copolymer of p-dioxanone with D,L-lactide having a weight average molecular weight of from 3,000 to 50,000, a copolymer of p-dioxanone with trimethylene carbonate having a weight average molecular weight of from 8,000 to 50,000 and a copolymer of p-dioxanone with $\epsilon$-caprolactone having a weight average molecular weight of from 10,000 to 100,000, or a mixture of two or more of them. Also preferred is a clayey and sticky substance which comprises a star-shaped copolymer having the aforementioned copolymers on its side chains (segmented copolymer), synthesized by mixing multifunctional alcohols such as glycerol, polyglycerol, pentaerythritol and star-shaped polyethylene glycol. In each of these clayey and sticky substances, the ratio of p-dioxanone occupying the copolymer is from 5 to 95 mol %.

The clayey and sticky substances comprising the above-described copolymers have such a degree of pressure sensitive adhesion that it can contact with a living body to temporarily fix it within the temperature range of from 30° C. or more which is close to the human skin temperature to the body temperature (40° C.) or less; for example, their adhesion strength when measured at 37° C. by the 90° peeling test of JIS Z 0237-1991 is approximately from 30 to 1,500 g (provided that the width of each sample is ½ inch, and therate of pulling is 300 mm/min).

This clayey and sticky substance is a relatively hard solid (rubber-like or solid wax-like in some cases) generally having no or slight stickiness at a temperature of lower than 30° C., but it softens and expresses plasticity at a temperature of about 30° C. or more which is the human skin temperature so that it can be easily deformed into optional shapes for example by finger pressure, and it has such a degree of shape holding ability that it does not fluidize and deform by its own weight at about 40° C. or less which is the human body temperature so that this is a kind of hot melt type sticky substance which increases its fluidity at the body temperature more and thereby changes its shape into a viscous substance such as starch syrup, paste or jelly. In this connection, this clayey and sticky substance softens to a Shore hardness of from 0 to 70 at 37° C.

In addition, since this clayey and sticky substance is a bioresorbable copolymer having a relatively low molecular weight as already described, it has an appropriate degradation absorption rate so that, as will be described later, it is markedly degraded within 2 to 3 weeks in the quicker case, or within 2 to 3 months in the slower case, after its contact with the body fluid in the living body. Thereafter, it disappears within 2 to 3 months in the quicker case, or within 6 to 12 months in the slower case, by its complete absorption in the living body and excretion from the body. However, the rate varies depending, for example, on the implanted region and implanted amount as a matter of course.

In this connection, examples of the prior art copolymers of p-dioxanone having the same combination (the ratio is different in some cases) of the monomers which form the copolymer of the present invention include (1) a copolymer of p-dioxanone with L-lactic acid for use in sutures, (2) a copolymer of p-dioxanone with c-caprolactone for use in sutures, (3) a copolymer of p-dioxanone with an alkylene carbonate for use in sutures and (4) a copolymer of p-dioxanone with a glycolide for use in degradable threads. These copolymers, however, are related to sutures having a relatively high molecular weight, developed with the aim of improve physical properties of polydioxanone using other monomers or, on the contrary, improving physical properties of a polymer comprised of the counterpart monomer by p-dioxanone, so that they are entirely different from the clayey and sticky substance of the present invention.

Next, the following describes the reasons for why the aforementioned copolymers having a relatively low molecular weight have the tackiness and plasticity matched to the object of the present invention within the already described temperature range.

As is well known, pressure-sensitive adhesives are viscoelastic materials that are liquids in themselves. Their glass temperatures (Tg) are −20 to 50° C., and their elastic moduli near room temperatuer are $10^5$ to $10^7$ dyn/cm$^2$. On the other hand, amorphous polymers show no distant periodicity in their molecular arrangement so that they are generally gum or liquid in the melted state above Tg, and those with smaller molecular weights change from the glass state to the melted state, in which they are viscous liquids. Their elastic moduli are $10^6$ to $10^7$ dyn/cm$^2$ in the semi-static gum state. The conditional change of such amorphous polymers from their viscous liquid (fluid) state to elastic solid state (sol→gel) is called gelation. Polymers which show stickiness at the stage of this gelation can be used as adhesive agents (substances).

In consequence, in order to obtain an adhesive agent (substance), a method is used in which molecules that are liquid at room temperature are polymerized into a polymer having a relatively low molecular weight or made into a gel by slightly cross-linking the polymers.

Natural water-soluble polysaccharides are generally called gum, which become a certain state of viscous hydrogel when water is contained therein. In addition, a large number of acrylic polymers as synthetic resins also form viscous hydrogel. However, it is not appropriate to use these polymers in adhesive agents (substances) as implants to be used in the living body, because they have not good biocompatibility and are lacking in safety and bioresobability.

As described above, it is an influential method to obtain an adhesive agent (substance) which expresses tackiness at the time of gelation just before solidification effected by segmental chains made of monomers which are liquid at ordinary temperature or from their oligomers as a low molecular polymer, but the adhesive agent (substance) must be flexible and have appropriate initial adhesive strength (tackiness) and peeling (adhesive) strength for the material to be adhered and its own cohesive force. That is, it must satisfy all of the initial adhesive strength (tackiness), adhesive force (adhesion) and cohesive force (cohesion) as the three requirements of adhesive agent (substance).

In addition to the above, the adhesive substance required by the present invention must completely or mostly satisfy such properties that it is relatively hard solid at about 30° C. or less, has tackiness, plasticity and shape holding ability at about 30 to 40° C. and is easily fluidized and deformed at 40° C. or more. That is, it must be a thermoplastic bioresorbable polymer which has such a gel point that it shows tackiness at about 30 to 40° C. Molecular chains in the thermoplastic adhesive polymer should not substantially form a three-dimensional network structure (which loses fluidity and plasticity) but have a two-dimensionally chain-elongated straight chain structure (which may have branched chains).

Design of a polymer which satisfies the aforementioned many conditions is a very difficult task which can be achieved finally by obtaining a number of factors such as the kind and number of monomers which constitute the copolymer, the sequence thereof and its molecular weight and distribution thereof.

The molecular designing of the present invention is described in the following further in detail.

In the case of a crystalline polymer which has such a molecular structure that it shows not only short distance but also long distance periodicity in the molecular chain due to strong intramolecular and intermolecular interaction, it cannot satisfy physical properties as a general adhesive agent (substance). That is, it is difficult to produce a substance which satisfies various characteristics as a clayey and sticky substance required by the present invention, from homopolymer having a low molecular weight at the time of gelation which occurs with the increment of molecular weight of polyglycolic acid or polylactic acid which is a bioresorbable crystalline polymer having such a strong intermolecular interaction that even a substance having a strength equal to or larger than the natural bone can be produced. In order to produce such a substance, it is necessary to prepare a copolymer constituted with bioresorbable monomers having poor periodicity due to randomization in the molecular structure.

Clinically usable monomers which can be used as a component of synthetic bioresorbable copolymers are not so many, which include glycolic acid (glycolide), L-, D- and D,L-lactic acid (lactide), p-dioxanone, ε-caprolactone and trimethylene carbonate. However, two-, three- or further multi-dimensional copolymers can be produced by combining these monomers. If these copolymers can show a viscous gel state within the range of relatively low molecular weight, it can be expected that a copolymer which satisfies the requirement as a clayey and sticky substance of the present invention and has appropriate bioresorbable properties can be selected therefrom. The present invention has been accomplished on the basis of such an idea.

In the case of a copolymer of polyglycolic acid with lactic acid, both monomers have so large intramolecular and intermolecular interaction in view of their molecular structures that the copolymer is a relatively hard solid during the stage of the increment of molecular weight from a lower level to a higher level and does not show properties as an adhesive agent (substance) by itself even when it is slightly softened by applying heat. In the same manner, other copolymers which contain glycolic acid as the main constituting component or still other copolymers which contain L- or D-lactic acid as the main constituting component also have large cohesion strength and no flexibility, so that they do not by themselves become clayey and sticky agents (substances) which serve the purpose of the present invention.

On the other hand, paradioxanone (p-DOX) is a condensed ring compound prepared from glycolic acid and ethylene glycol, and polyparadioxanone obtained by its ring-opening polymerization is an alternating or random copolymer in which the sequence of glycolic acid having markedly large cohesion strength is disturbed by ethylene glycol having relatively small cohesion strength alternatively (in the case of head-to-tail polymerization) or randomly (mixture of head-to-head, tail-to-tail and head-to-tail polymerization) and is therefore a rubber-like soft solid polymer even at a relatively large molecular weight in spite of the fact that polyglycolic acid and polyethylene glycol can produce crystalline hard (particularly polyglycolic acid) homopolymers. In addition, caprolactone having a low molecular weight is a wax-like solid polymer within a range of molecular weight by which it becomes solid. In the same manner, trimethylene carbonate forms a wax- or rubber-like soft solid polymer. The reason for forming soft homopolymers from these monomers is that intramolecular interaction by the molecular structure of each monomer itself and intermolecular interaction between the polymer molecules are not stronger than the case of crystalline polymers. However, though these materials are high molecular compounds having a relatively low molecular weight at the time of gelation, they have no sufficient conditions to be used as clayey and sticky agents (substances) unfortunately.

Thus, in order to produce an adhesive agent (substance), it is necessary to think out a means for synthesizing a copolymer which is constituted by the aforementioned monomers having relatively low molecular weight in which the molecular sequence is further disturbed. In addition, a copolymer as the clayey and sticky substance of the present invention to be used in the living body should have the following properties 1) to 4).

1) It can well adhere to the living bodies (soft tissues and bones wet with the body fluid) by proper "mellowing". The adhesive strength may be as large as possible as long as it is removable.

2) It has appropriate affinity, but with proper balance of hydrophilic and hydrophobic properties so that it does not flow out by easily dissolved in the body fluid (appropriately amphipatic).

3) It can perform plastic deformation at from the skin temperature to the body temperature but has a viscosity enough to hold its shape to such a degree that it does not fluidize and flow out from the adhered surface. It may be a hot melt type which is solid at ordinary temperature but shows strong tackiness by fluidization when heated.

4) It can show proper degradation rate in the living body, and its adhesive strength can be maintained during the period until the affected part is healed, but it should disappear after the healing by its relatively quick degradation and absorption (the tackiness may be disappeared during the resorption stage after healing, but the adhesive strength can be maintained by the reduction of molecular weight). In the quicker case, the copolymer is significantly degraded until 2 to 3 weeks after the treatment and absorbed and disappeared by 2 to 3 months and excreted from the living body. Even in the slower case, it is desirable that the copolymer is significantly degraded until 2 to 3 months after the treatment and absorbed and disappeared by 6 to 12 months and excreted from the living body.

In order to obtain a clayey and sticky substance which can satisfy the aforementioned conditions, the present inventors have synthesized various copolymers by combining the aforementioned bioresorbable monomers and examined their requirement, and found as the results that the clayey and sticky substance which satisfies the gist of the present invention is a low polymerization degree compound that contains p-dioxanone as a component of the copolymer (weight average molecular weight is within the range of from 2,000 to 100,000), particularly any one of a copolymer of p-dioxanone with D-lactic acid having a weight average molecular weight of from 2,000 to 40,000, a copolymer of p-dioxanone with L-lactic acid having a weight average molecular weight of from 2,000 to 40,000, a copolymer of p-dioxanone with D, L-lactic acid having a weight average molecular weight of from 3,000 to 50,000, a copolymer of p-dioxanone with trimethylene carbonate having a weight average molecular weight of from 8,000 to 50,000 and a copolymer of p-dioxanone with ε-caprolactone having a weight average molecular weight of from 10,000 to 100,000, or a star-shaped copolymer which has the aforementioned copolymer mixed with a functional alcohol as a branched chain.

The aforementioned copolymer can be synthesized by utilizing the conventional process. For example, p-dioxanone and other copolymer components are mixed with an appropriate initiator (e.g., lauryl alcohol) and a catalyst (e.g., 2-ethylhexane tin, di-n-butyltin dilaurate), effecting copolymerization at 120 to 180° C. for 1 to 20 hours, and repeating purification steps with solvents several times.

The term "star-shaped copolymer" as used herein means a segmented copolymer which comprises a core of a polyfunctional alcohol and the aforementioned copolymers as segment chains substitited at the hydroxyl groups of the polyfunctional alcohols. The molecule of such segmented copolymer has a star-like shape.

Since p-dioxanone is a dehydration condensation product of glycolic acid and ethylene glycol, these copolymers are essentially three-dimensional copolymers. Structural formula of a copolymer of p-dioxanone with D-, L- or D,L-lactic acid is as shown in the following formula (1), structural formula of a copolymer of p-dioxanone with trimethylene carbonate is as shown in the following formula (2) and structural formula of a copolymer of p-dioxanone with ε-caprolactone is as shown in the following formula (3). When the copolymer of the following formula (1) is a mixture of D-form and L-form, it can be regarded as a quaternary copolymer.

(1)

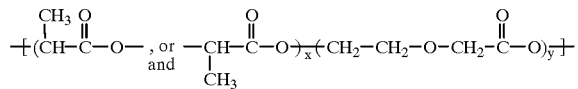

(In the formula, x and y are positive integers.)

(2)

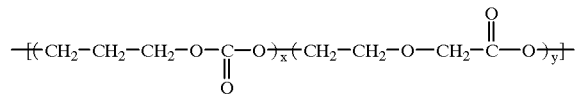

(In the formula, x and y are positive integers.)

(3)

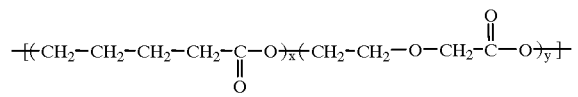

(In the formula, x and y are positive integers.)

These copolymers obtained by using a condensation product of glycolic acid and ethylene glycol, namely p-dioxanone, as the main component and copolymerizing it with D-, L- or D,L-lactic acid, or trimethylene carbonate or ε-caprolactone are basically ternary copolymers or three- or more-component copolymers further copolymerized with these monomers, which have disturbed molecular sequences, not so large cohesion strength and a relatively small weight average molecular weight of approximately from 2,000 to 100,000, so that they show flexibility and free plastic deformation ability within the temperature range of from 30° C. or more which is close to the human skin temperature to 40° C. or less which is close to the body temperature. Also, they have such a degree of tackiness that living tissues can be temporarily fixed through their adhesion, and they can be formed into optional shapes easily and freely by deforming them for example by the finger pressure. In addition, since these copolymers are changed into viscous polymers having increased fluidity at 40° C. or more, they have advantages in that an operation for injecting them into damaged parts of the living body can be carried out easily, and other additives can be formulated and mixed easily at the site of operation.

Next, the reasons why paradioxanone (p-DOX) is an essential component as a component of the copolymer of the present invention and why its copolymers with other monomers are necessary as the clayey and sticky substance of the present invention are described in the following more in detail.

As described in the foregoing, paradioxanone (p-DOX) is a dehydration condensation product of glycolic acid and ethylene glycol, and polyparadioxanone can be synthesized by its ring-opening polymerization. since this is a copolymer (alternating or random copolymer), periodical molecular sequence is disturbed and its intramolecular and intermolecular interaction becomes smaller than the case of polyglycolic acid of glycolic acid alone. This is because cohesion strength of the constituting molecules of polyethylene glycol (PEG) is smaller than that of polyglycolic acid (PGA). That is, cohesion energies of the PSA-constituting —$CH_2$—and —CO—O—are 0.68 kcal/mol and 2.9 kcal/mol, respectively, and those of the PEG-constituting —CH2— and —O—are 0.68 kcal/mol and 1.0 kcal/mol, respectively. In describing again, when PGA homopolymer becomes EG-mediated copolymer, its sequence is disturbed and intermolecular and intramolecular cohesion strength of the polymer are reduced by EG. However, even if polyparadioxanone has a low molecular weight, its cohesion strength is still too high to be used as the adhesive substance of interest of the present invention.

Since melting point (mp) of paradioxanone as a monomer is 94 to 96° C., it is solid at ordinary temperature. Polyparadioxanone (homopolymer) obtained by polymerization of the monomer at the melting point or more is solid even at a relatively low molecular weight (up to several thousands) and is not a soft substance which becomes an adhesive substance by hot melting at a low temperature of about 50° C. This fact supports that paradioxanone is not suited for obtaining an adhesive substance within a low molecular weight range because of its unsuitable cohesion strength. On the other hand, polyglycolic acid obtained by polymerizing glycolide (mp: 83–85° C.) has larger cohesion than that of polyparadioxanone and is a hard oligomer which does not become an adhesive soft substance even within a low molecular weight range.

It is a well known fact that, similar to the case of polyglycolic acid, polyparadioxanone is a polymer which has excellent biocompatibility and is degraded and absorbed in the living body and excreted therefrom. It is known that degradation of polyparadioxanone is slower than that of polyglycolic acid but faster than that of poly-D,L-lactic acid and more faster than that of the homocopolymer of L-lactic acid or D-lactic acid. Because of this, it is reasonable to synthesize and evaluate paradioxanone copolymers in designing the adhesive substance of the present invention which is mostly degraded in the living body within 2 to 3 months and completely absorbed and disappeared after about six months. In that case, other monomers of such copolymers should have such properties that not only they can disturb the molecular sequences but also they can give appropriate intramolecular and intermolecular interaction and add physical properties as the intended adhesive substance of the present invention under a relatively low molecular weight amorphous condition. In addition, they also must have an effect to control their degradation and absorption rates in the living body within appropriate ranges.

On the basis of such considerations, the present inventors have copolymerized p-dioxanone with monomers which have been used in the practical field as implantation materials in the living body, such as L-lactic acid, D-lactic acid, D,L-lactic acid (mixture of D- and L-isomers), trimethylene carbonate (TMC) and $\epsilon$-caprolactone ($\epsilon$-CL) and have succeeded as the result in obtaining the clayey and sticky substance of the present invention which is bioresorbable within the aforementioned range of molecular weight. In addition, it was found that degree of adhesive strength of the copolymer at around the body temperature (37° C.) which proves the magnitude of cohesion is roughly in the order of L-lactic acid=D-lactic acid>D,L-lactic acid>TMC>$\epsilon$-CL. The lactic acid segment is the most useful monomer for obtaining a clayey and sticky substance best suited for the object, because the presence of —$CH_3$ in its side chain is effective in reducing intermolecular force and adding more appropriate tackiness and the ester bond is effective in properly keeping reduction of intramolecular and intermolecular interaction in the sequence disturbed by the copolymerization.

In that case, since the direction of —$CH_3$ in the L-isomer (D-isomer) is stipuated in each side of the main chain, higher cohesion strength can be obtained than the case of D,L- in which the direction of —$CH_3$ is inversively situated each other, so that it shows generally high adhesion, hardness and shape holding ability.

Since trimethylene carbonate (TMC) contains three —$CH_2$—groups in the main chain, it shows paraffin-like properties by their effects, so that adhesive substance superior to the lactic acid group cannot be obtained. Also, since hydrolysis of the carbonate bond is not faster than the case of ester bond, degradation rate of a copolymer which contains this monomer is slower than that of the lactic acid group.

Since $\epsilon$-caprolactone ($\epsilon$-CL) contains five low cohesion energy —$CH_2$—groups, movement of molecular chain is easy and it is fairly flexible. In consequence, a copolymer containing this monomer is a clayey and sticky substance depending on the copolymerization ratio even with a high molecular weight (MW: 100, 000) . However, it becomes lipophilic due to the hydrophobic effect of the non-polar —$CH_2$—in view of its balance with —CO—, so that its wettability with moisture-containing living bodies is not good. This, however, is effective when certain clayey and sticky substances which do not require adhesion too much and are slow in degradation, such as filling or plugging materials, are required.

In this connection, the present inventors have synthesized various copolymers by respective combinations of trimethylene carbonate (TMC, mp: 47–49° C.), L-lactic acid (D-lactic acid) (L-lactide, D-lactide, mp: 95–97° C.), D,L-lactic acid (D,L-lactide, meso-lactide, mp: 124–126° C.), glycolic acid (glycolide, mp: 83–85° C.) and $\epsilon$-caprolactone ($\epsilon$-CL: mp: -6—-4° C.), excluding paradioxanone (p-DOX) which has actual results as a monomer that constitutes bioresorbable synthetic polymers. For example, these copolymers were trimethylene carbonate/D,L-lactic acid, trimethylene carbonate/L-lactic acid, trimethylene carbonate/$\epsilon$-caprolactone, glycolic acid/L-lactate, glycolic acid/D,L-lactic acid, glycolic acid/trimethylene carbonate, glycolic acid/$\epsilon$caprolactone, D,L-lactic acid/$\epsilon$-caprolactone and L-lactic acid/ $\epsilon$caprolactone. Low molecular weight (several hundreds to several thousands) range polymers of these monomers were also synthesized (there is no use in synthesizing high molecular weight polymers which do not become clayey and sticky substances). However, it was not able to find a polymer having the physical and chemical properties required by the present invention and showing appropriate rates of bioresorption. This fact justifies the standpoint of the present invention for molecular designing which uses p-DOX as a component of copolymers.

As already described, the ratio of p-dioxanone occupying the copolymer is from 5 to 95 mol %. Tackiness and other physical properties of the copolymer become substantially the same as the properties of the homopolymer of p-dioxanone when the ratio of p-dioxanone exceeds 95 mol %, and physical properties of the copolymer become substantially the same as the properties of homopolymers of other copolymer components when the ratio of p-dioxanone is smaller than 5 mol %, so that they do not become adhesive substances which satisfies the object of the present invention. The ratio of p-dioxanone is more preferably from 15 to 85 mol %, most preferably from 30 to 60 mol %. A copolymer which contains p-dioxanone within this range shows proper tackiness and unrestricted plasticity within a temperature range of from 30 to 40° C. It also shows practical shape holding ability even at 37° C. which is the normal body temperature.

Also as described in the foregoing, weight average molecular weight of the copolymer is within the range of from 2,000 to 100,000, and when it exceeds 100,000, the copolymer loses flexibility and its tackiness and plasticity are reduced even at a temperature of 30° C. or more, which are inconvenient. It also causes prolongation of time necessary for bioresorption of the copolymer in the living body. On the other hand, when the weight average molecular weight is smaller than 2,000, the copolymer becomes nealy liquid, which is inconvenient because its stickiness becomes excess and its ropiness causes and its shape holding ability becomes poor and its original shape is lost due to its spontaneous fluidization by its own weight. However, the aforementioned molecular weight range may be the range of the copolymer single body, or of an assembly of copolymers combined with a larger molecular weight than this range or simultaneously with more smaller molecular weight, but it may be suitable enough if their average molecular weight is experimentally within the range of approximately from 2,000 to 100,000. The range of molecular weight of individual copolymer is as described in the foregoing. In this case, the lower limit weight average molecular weight of 2,000 also has the following meaning. That is, when various types of additives described in the foregoing are added to the adhesive substance, its adhesion characteristics are reduced in general. The weight average molecular weight of 2,000 means the lower limit by which appropriate tackiness and clayey property can be reformed by adding additives even to an adhesive substance which has some of the aforementioned disadvantages to some extent without additive.

The clayey and sticky substance of the present invention comprised of the aforementioned copolymer may be further mixed with a poly-p-dioxanone having a weight average molecular weight larger than that of the copolymer. When a p-dioxanone homopolymer is mixed in this manner, shape holding ability of the adhesive substance is improved so that it can avoid the problem of causing migration of the substance in the living body by losing its shape due to its fluidization at the body temperature. It also can slow down the whole degradation rate a little.

The poly-p-dioxanone to be mixed may preferably have a weight average molecular weight of roughly 100,000 or less, because mixing of poly-p-dioxanone having more higher molecular weight will cause an inconvenience of requiring unnecessarily prolonged period of time for total resorpotion It is desirable to set the mixing ratio of this poly-p-dioxanone within the range of from 5 to 30% by weight. When it is mixed in an amount of larger than 30% by weight, it will result in the just described inconvenience regarding the degradation and absorption steps, as well as decreasing of tackiness and plastic deformation ability, and its mixing effects will not substantially be obtained when it is mixed in an amount of less than 5% by weight.

In addition, the clayey and sticky substance of the present invention may be made into a porous body by including innumerable bubbles therein. When bubbles are included in this manner, the body fluid can penetrate easily into inside of the clayey and sticky substance through the bubbles when the substance is used in the living body so that hydrolysis of the clayey and sticky substance can be effected quickly, and the peripheral tissue cells are transferred into inside of the clayey and sticky substance together with the body fluid and grow therein so that the tissues can be reconstructed quickly.

The most simple and easy method for including bubbles is to include air by thoroughly kneading the clayey and sticky substance with fingertips. In another method, air is included by dissolving the adhesive substance in a solvent, precipitating the substance in the non-solvent and then evaporating the solvent. Still another method is to mix the adhesive substance with powder of porous bioceramics.

As described in the foregoing, at a temperature of from 30 to 40° C., the bioresorbable clayey and sticky substance of the present invention shows proper tackiness for living tissues and a plastic deforming ability which renders possible easy and unrestricted change of shape of the substance with finger pressure, so that it can be used in the following various applications.

Firstly, it can be used as a hemostatic material for stopping bleeding from the bone marrow by adhering the adhesive substance to the bone marrow instead of the conventionally used bone wax. It can also be used as a hemostatic material of soft tissues by kneading the adhesive substance in a bleeding region of a soft tissue of the living body.

When the adhesive substance is used as a hemostatic material in this manner, it may be an effective method to include at least one of blood coagulation factors, drugs, cellulose oxide fibers, gelatin sponge and micro-fibrous collagen, which are effective in stopping bleeding, in an appropriate amount in the adhesive substance. These additives may be included in the adhesive substance in advance, but it is more simple and easy to include them while the adhesive substance is kneaded by fingertips of a surgeon intraoperatively, thereby effecting adjustment of its hardness, tackiness and shape holding ability. In this case, the content of these additives is not particularly limited but preferably 60% by weight or less, because tackiness and flexibility of the adhesive substance are spoiled if they are included in too much amount.

Secondly, when bones are connected using artificial osteosynthetic plates or screws, the biodegradable polymeric clayey and sticky substance can be used as an adhesion material for their temporary fixation by inserting the adhesive substance between adhering surfaces of the bones. Also, when an incised part of a soft tissue such as muscle or skin is stitched with a suture, the adhesive substance can be used as an adhesion material for the temporary fixation of connected or overlapped parts of the soft tissue by inserting it into the incised part.

When the adhesive substance is used as an adhesion material of hard tissues or soft tissues in this manner, it may be significant to include at least one of bioactive ceramics powder, various types of cytokine, derivatives of chitin or chitosan, various types of drugs and hormones and other bioresorbable polymers in the adhesive substance. Though the adhesion material is changed into a clayey material with low stickiness when these additives are included in a large amount, its deformation can be effected at will by finger pressure so that the object of the present invention can be attained, When the adhesive substance is used in hard tissues by including bioceramics powder, the adhesive material and bones are strongly connected via calcium phosphate precipitated on the surface due to the bone conduction of bioceramics. Also, hydrolysis of the adhesive substance is accelerated in some cases. When BMP or a chitin or chitosan derivative as a bone growth factor and bioceramics are included, they exert an advantage in that connection of bones can be achieved within more shorter period of time due to acceleration of the propagation of osteoblasts and growth of bone tissues inside the adhesive material. In addition, inclusion of hyaluronic acid is effective for the regeneration of tissues, because its effect to accelerate penetration of blood vessels can be expected.

Examples of the bioceramics powder to be used include those which are bioactive, such as sintered hydroxyapatite, bioglass, ceravital, apatite wollastonite glass ceramics, wet (un-sintered) hydroxyapatite, tricalcium phosphate, tetracalcium phosphate, dicalcium phosphate and calcite, and examples of the cytokine to be used include TGF-β (transforming growth factorβ), EGF (epidermal growth factor), TGF (fibroblast growth factor), $IFN_m$ (various types of interferon), $LAF_m$ (various types of interleukin) and $BHP_m$ (various types of bone growth factor) . Examples of the drugs to be included are cited in the following. These drugs may be used by selecting known effective content and ratio (%).

Examples of rheumatoid-treating drugs include anti-rheumatoid drugs, steroid drugs and immunosuppressants, examples of osteoporosis-treating drugs include calcium preparations, active vitamin D (derivative), vitamin $K_2$, calcitonin, ipriflavone, estrogen, diphosphonic acid derivatives, parathyroid hormone, novel steroid derivatives and bone morphogenetic protein, and examples of anticancer agents include adriamycin, cisplatin, mitomycin and 5-fluorouracil. Also included are antibacterial agents and antibiotics. since the adhesive substance which contains these drugs can control release of the drugs by gradual degradation of its base material, it basically forms a drug delivery system (DDS).

Thirdly, the clayey and sticky substance can also be used as an adhesive material for use in temporary fixing implant materials made of metals, ceramics or high polymer materials mutually or as an adhesive material for use in temporary fixing implant materials to living tissues. That is, it can be used to assist the fixation by inserting it into a narrow gap between a plate and a screw or between a plate and a bone. In the absence of a substance to fill up such a gap, un-contacted part between the plate and bone generates considerable "loosening" triggered by the movement of the bone and causes disconnection and deformation of devices, but such fai;ts can be avoided by the filling of the adhesive substance.

Fourthly, since plastic deformation of the adhesive substance can be made at will in three-dimensional directions at a temperature of from 30° C. which is close to the human skin temperature to the body temperature (40° C.), the adhesive substance can be used as a prosthetic material or filler for use in tissue reconstruction by deforming the adhesive substance into a shape completely identical to the shape of a steric defect of living tissues and adhering and fixing it to steric defect. That is, when the adhesive substance or a clayey substance is applied and fixed to the steric defect, said adhesive substance is hydrolyzed by its contact with the body fluid and disappears while being replaced by newly growing tissue, so that the tissue of the steric defect is restored to its original shape and completely reconstructed.

When the adhesive substance is used as a prosthetic material or filler for tissue reconstruction, it may contain at least one of bioactive bioceramics powder, cytokine, derivatives of chitin or chitosan, certain drugs, various growth factors, living bone fragments, cartilage fragments, soft tissues and other bioresorbable polymers. Advantages of the use of bioceramics powder, derivatives of chitin or chitosan, bone growth factors and drugs are as described in the foregoing, and cytokine is also effective in effecting growth and restoration of the soft tissue of interest. In addition, inclusion of fragments such as bone fragments and cartilage fragments has an advantage in quickly reconstructing defects of bone, cartilage or soft tissue.

Fifthly, since the clayey and sticky substance can be mixed with the aforementioned substances for treatment and reconstruction use without using a mixing solvent but simply kneading them after slight heating at about the body temperature, drugs (such as cytokine and hormones) or synthetic drugs (anticancer agents and carcinostatic agents), which are apt to undergo denaturation and deterioration by solvents or heat, can be mixed and prepared easily under stable conditions at desired optional ratio at the site of surgical operation, so that it can be used as a drug delivery system (DDS) carrier which can be mixed unrestrictedly at will with a sustained release preparation capable of gradually releasing a drug by self-degradation of the preparation.

Sixthly, this clayey and sticky substance can be used as a material for temporary scaffold for use in tissue engineering such as a case in which reconstruction of a lost tissue is carried out by propagating cells collected from the tissue In vitro and then returning the propagated cells to the tissue.

Seventhly, when the clayey and sticky substance has good fluidity at a temperature of from 40 to 50° C. which is not so greatly higher than the body temperature, it can be used as a filling or plugging material which is gradually replaced by a natural bone when it is put into a syringe, heated to such temperature and then injected into a defect or crack of the bone.

Eighthly, the clayey and sticky substance can be used as an accretion-preventing material by heating and rolling it with finger pressure to deform it from a film of several ten pm to a sheet of several hundred am or more and applying the thus prepared Material on a damaged region.

When the adhesive substance is used as a framework for cell technology, a plugging material, or a conglutinant prevention agent, it may include at least one of bioactive bioceramics powder, various types of cytokine, derivatives of chitin or chitosan, various types of drugs and hormones and other bioresorbable polymers in the adhesive substance. The advantages of these addtional components are as described above.

Examples of the present invention are given below by way of illustration and not by way of limitation.

EXAMPLE 1

Synthesis of p-DOX/TMC Copolymer

A 10.2 g (0.1 mol) of p-dioxanone (p-DOX) and a 10.2 g (0.1 mol) of trimethylene carbonate (TMC) were put into a glass vessel, 300 ppm of lauryl alcohol as an initiator and 100 ppm of 2-ethylhexane tin as a catalyst were dispersed in toluene and added to the above compounds, and then toluene was evaporated under a reduced pressure and the resulting residue was further treated under a reduced pressure for 20 hours to remove toluene completely. After replacement of air with $N_2$ by its purging, the glass vessel again decompressed was sealed.

This vessel was set in an oil bath of 140° C., and 2 hours of polymerization reaction was carried out while stirring the contents. Thereafter, a purification step in which the reaction mixture is dissolved in acetone and then precipitated in ethanol was repeated several times to obtain a p-DOX/TMC copolymer (No. 1).

Other p-DOX/TMC copolymers (No. 2 to No. 4) were obtained in the same manner except that the reaction time changed to 8, 12 or 16 hours, respectively.

Reaction time, weight average molecular weight, properties and Shore hardness at 37° C. of these p-DOX/TMC copolymers No. 1 to No. 4 are shown in Table 1.

TABLE 1

| No. | Reaction time (hr) | $\overline{Mw}$* | Properties | Hardness (37° C.) |
|---|---|---|---|---|
| 1 | 2 | 7,500 | White waxy with tackiness, colorless transparent liquid when heated (55° C.). | 0 |
| 2 | 8 | 15,000 | Colorless transparent like starch syrup with large tackiness (stickiness), fluidity increases when heated (55° C.). | 0 |
| 3 | 12 | 29,000 | Colorless transparent soft clay with slightly tackiness, changes to a starch | 5.9 |

TABLE 1-continued

| No. | Reaction time (hr) | $\overline{Mw}$* | Properties | Hardness (37° C.) |
|---|---|---|---|---|
| | | | syrup-like stale and generates tackiness when heated (55° C.). | |
| 4 | 16 | 42,500 | The same as the above. | 6.2 |

*Weight average molecular weight

EXAMPLE 2

Synthesis of p-DOX/D,L-lactic Acid Copolymer

A 10.2 g (0.1 mol) of p-dioxanone (p-DOX) and 14.4 g (0.1 mol) of D,L-lactic acid were put into a glass vessel, 300 ppm of lauryl alcohol as an initiator and 100 ppm of 2-ethylhexane tin as a catalyst were dispersed in toluene and added to the above compounds, and then toluene was evaporated under a reduced pressure and the resulting residue was further treated under a reduced pressure for 20 hours to remove toluene completely. After replacement of air with $N_2$ by its purging, the glass vessel again decompressed was sealed.

This vessel was set in an oil bath of 150° C., and 2 hours of polymerization reaction was carried out while stirring the contents. Then, a purification step in which the reaction mixture is dissolved in acetone and then precipitated in ethanol was repeated several times to obtain a p-DOX/D,L-lactic acid copolymer (No. 5).

Other p-DOX/D,L-lactic acid copolymers (No. 6 and No. 7) were obtained in the same manner except that the reaction time was changed to 3 or 7 hours. Also, other p-DOX/D,L-lactic acid copolymers (No. 8 and No. 9) were obtained in the same manner except that the reaction time was fixed to 7 hours and the mixing molar ratio of p-DOX and D,L-lactic acid was changed to 2:1 or 3:1.

Reaction time, molar ratio of p-DOX and D,L-lactic acid, weight average molecular weight, properties and Shore hardness at 37° C. of these p-DOX/D,L-lactic acid copolymers No. 5 to No. 9 are shown in Table 2.

TABLE 2

| No. | p-DOX: D,L-LA | Reaction time (hr) | $\overline{Mw}$* | Properties | Hardness (37° C.) |
|---|---|---|---|---|---|
| 5 | 1:1 | 2 | 9,600 | Soft clayey substance with high tackiness and liquid state when heated (55° C.). | 0 |
| 6 | 1:1 | 3 | 12,000 | Clayey substance which easily deforms by finger pressure, changes to a starch syrup-like state and generates high tackiness by softening when heated (55° C.). | 20 |
| 7 | 1:1 | 7 | 21,200 | Hard plastic-like substance which slightly deforms by finger pressure and generates tackiness by softening when heated (55° C.). | 70 |
| 8 | 2:1 | 7 | 24,100 | Similar to No. 6, but its stickiness further increases when heated. | 8.1 |

TABLE 2-continued

| No. | p-DOX: D,L-LA | Reaction time (hr) | $\overline{Mw}$* | Properties | Hardness (37° C.) |
|---|---|---|---|---|---|
| 9 | 3:1 | 7 | 28,100 | Shows properties of No. 5 and No. 6 and is soft. | 0 |

*Weight average molecular weight

EXAMPLE 3

Synthesis of p-DOX/ε-CL Copolymer

A 10.2 g (0.1 mol) of p-dioxanone (p-DOX) and 11.4 g (0.1 mol) of ε-caprolactone (ε-CL) were put into a glass vessel, 300 ppm of lauryl alcohol as an initiator and 100 ppm of 2-ethylhexane tin as a catalyst were dispersed in toluene and added to the above compounds, and then toluene was evaporated under a reduced pressure and the resulting residue was further treated under a reduced pressure for 20 hours to remove toluene completely. After replacement of air with $N_2$ by its purging, the glass vessel again decompressed was sealed.

This vessel was set in an oil bath of 150° C. to carry out 2 hours of polymerization reaction while stirring the contents, and then the polymerization vessel was put out to terminate the reaction. Thereafter, a purification step in which the reaction mixture is dissolved in acetone and then precipitated in ethanol was repeated several times to obtain a p-DOX/ε-CL copolymer (No. 10).

Other p-DOX/ε-CL copolymers (No. 11 and No. 12) were obtained in the sane manner except that the reaction time was changed to 3 or 7 hours.

Reaction time, weight average molecular weight, properties and Shore hardness at 37° C. of these p-DOX/ε-CL copolymers No. 10 to No. 12 are shown in Table 3.

TABLE 3

| No. | Reaction time (hr) | $\overline{Mw}$* | Properties | Hardness (37° C.) |
|---|---|---|---|---|
| 10 | 2 | 15,600 | Liquid with high stickiness, viscosity is reduced markedly when heated (55° C.). | 0 |
| 11 | 3 | 32,000 | Starch syrup form with high stickiness and becomes liquid and fluidizes when heated (55° C.). | 0 |
| 12 | 7 | 55,300 | Soft clayey form with tackiness present and changes to liquid and fluidizes when heated (55° C.). | 0 |

*Weight average molecular weight

EXAMPLE 4

Synthesis of p-DOX/L-lactic Acid Copolymer p-Dioxanone (p-DOX) and L-lactic acid were put into a glass vessel at a mixing molar ratio of 1:1, 300 ppm of it lauryl alcohol as an initiator and 100 ppm of 2-C, ethylhexane tin as a catalyst were dispersed in toluene and added to the above compounds, and then toluene was evaporated under a reduced pressure and the resulting residue was further dried under a reduced pressure for 20 hours to remove toluene completely. After replacement of air with $N_2$ by its purging, the glass vessel again decompressed was sealed.

This vessel was set in an oil bath of 150° C. to carry out 7 hours of copolymerization reaction while stirring the contents, and then the polymerization vessel was taken out to terminate the reaction. Thereafter, a purification step in which the reaction mixture is dissolved in acetone and then precipitated in ethanol was repeated several times to obtain a p-DOX/L-lactic acid copolymer (No. 13).

Other p-DOX/L-lactic acid copolymers (No. 14 No. 15) were obtained in the same manner except that the mixing molar ratio of p-DOX and L-lactic acid was changed to 2:1 or 3:1.

Reaction time, mixing molar ratio of p-DOX and L-lactic acid, weight average molecular weight, properties and shore hardness at 37° C. of these p-DOX/L-lactic acid copolymers No. 13 to No. 15 are shown in Table 4.

TABLE 4

| No. | p-DOX: L-LA | Reaction time (hr) | $\overline{Mw}$* | Properties | Hardness (37° C.) |
|---|---|---|---|---|---|
| 13 | 1:1 | 7 | 24,000 | Hard plastic-like substance which slightly deforms by finger pressure, and generates tackiness by softening when heated (55° C.). | 22.5 |
| 14 | 2:1 | 7 | 25,100 | Soft clayey substance which easily deforms by finger pressure, shows slight tackiness which increases by softening and changing to a starch syrup-like state when heated (55° C.). | 1.0 |
| 15 | 3:1 | 7 | 25,100 | Clayey substance softer than No. 14, which easily deforms by finger pressure, shows tackiness which increases by softening and fluidizing when heated (55° C.). | 0 |

*Weight average molecular weight

EXAMPLE 5

Synthesis of Star-shaped Copolymer p-Dioxanone (p-DOX) and trimethylene carbonate (TMC) were put into a glass vessel at a mixing molar ratio of 1:1, 0.001 mol % of pentaerythritol was added thereto, 300 ppm of lauryl alcohol as an initiator and 100 ppm of 2-ethylhexane tin as a catalyst were dispersed in toluene and added to the above compounds, and then toluene was evaporated under a reduced pressure and the resulting residue was further treated under a reduced pressure for 20 hours to remove toluene completely. After replacement of air with $N_2$ by its purging, the glass vessel again decompressed was sealed.

This vessel was set in an oil bath of 140° C. to carry out 7 hours of copolymerization reaction while stirring the contents, and then the polymerization vessel was taken out to terminate the reaction. Thereafter, a purification step in which the reaction mixture is dissolved in acetone and then precipitated in ethanol was repeated several times to obtain a star-shaped p-DOX/TMC copolymer (No. 16).

Another star-shaped p-DOX/TMC copolymer (No. 17) was obtained in the same manner except that the mixing molar ratio of p-DOX and TMC was changed to 2:1.

Next, a star-shaped p-DOX/D,L-lactic acid copolymer (No. 18) was obtained in the same manner except that p-dioxanone (p-DOX) and D,L-lactic acid were put into a glass vessel at a mixing molar ratio of 1:1, and the oil bath temperature was changed to 150° C. In the same manner, another star-shaped p-DOX/D,L-lactic acid copolymer (No. 19) was obtained by changing the mixing molar ratio of p-dioxanone (p-DOX) and D,L-lactic acid to 2:1.

Reaction time, mixing molar ratio, weight average molecular weight, properties, shore hardness at 37° C. and adhesion of these star-shaped copolymers No. 16 to No. 19 are shown in Table 5. In this case, the adhesion is a value measured at an atmosphere of 37° C. by the 90° peeling test of JIS Z 0237-1991 (provided that the width of each sample is ½ inch, and the stress rate is 300 mm/min).

TABLE 5

| No. | p-DOX: TMC | Reaction time (hr) | $\overline{Mw}$* | Properties | Hardness (37° C.) | Adhesion (37° C.) (g) |
|---|---|---|---|---|---|---|
| 16 | 1:1 | 7 | 16,000 | Fluid polymer, tacky, becomes liquid when heated (55° C.). | 0 | 100 |
| 17 | 2:1 | 7 | 7,000 | White soft waxy polymer which is apt to flow, tacky, changes to liquid when heated (55° C.). | 0 | 40 |

| No. | p-DOX: D,L-LA | Reaction time (hr) | $\overline{Mw}$* | Properties | Hardness (37° C.) | Adhesion (37° C.) (g) |
|---|---|---|---|---|---|---|
| 18 | 1:1 | 7 | 13,000 | Hard clayey polymer which easily deforms by finger pressure, softens and generates tackiness when heated (55° C.). | 9.5 | 500 |
| 19 | 2:1 | 7 | 9,800 | Clayey substance which easily deforms by finger pressure, shows tackiness which increases by softening and changing to a starch syrup-like state when heated (55° C.). | 0 | 160 |

*Weight average molecular weight

EXAMPLE 6

In the same manner as described in Example 2, p-dioxanone (p-DOX) and D,L-lactic acid were allowed to undergo 7 hours of reaction at a mixing molar ratio of 3:1 to obtain a p-DOX/D,L-lactic acid copolymer having a weight average molecular weight of 28,100.

This copolymer was kneaded with 25 or 50% by weight of hydroxyapatite (HA) having an average particle size of 5 μm to obtain mixtures a and b. In addition, this copolymer was kneaded with 60% by weight of the above-described hydroxyapatite (HA) and 3% by weight of hyaluronic acid to obtain a mixture c.

Properties and Shore hardness at 37° C. of the copolymer and its mixtures a, b and c are shown in Table 6.

TABLE 6

| Mixture | Mixing ratio of HA (wt %) | Properties | Hardness (37° C.) |
|---|---|---|---|
| Copolymer only | 0 | Soft clayey substance which easily deforms by finger pressure, shows tackiness which increases by softening and changing to a starch syrup-like state when heated (55° C.). | 0 |
| a | 25 | Clayey substance, hardens due to mixing of HA, tackiness is reduced, deforms with the passage of time by its own weight, tackiness increases by softening when heated (55° C.). | 10 |
| b | 50 | Clayey substance, hardens due to mixing of large amount of HA, almost no tackiness, no deformation by its own weight, tackiness is generated by softening when heated (55° C.). | 33 |

| Mixture | Mixing ratio of HA and hyaluronic acid (wt %) | Properties | Hardness (37° C.) |
|---|---|---|---|
| c | HA:60 Hyaluronic acid: 3 | Hard clayey substance which softens but does not generate tackiness when heated (55° C.), tackiness is generated slightly when water is contained. | 47 |

EXAMPLE 7

The p-DOX/D,L-lactic acid copolymer having a weight average molecular weight of 28,100 obtained in Example 6 was kneaded with 25 or 50% by weight of carboxymethyl chitin (CM chitin) powder to obtain mixtures d and e.

Properties, Shore hardness at 37° C. and swelling ratio of the copolymer and its mixtures d and e are shown in Table 7.

TABLE 7

| Mixture | Mixing ratio of CM chitin (wt %) | Properties | Hardness (37° C.) | Swelling ratio (times) |
|---|---|---|---|---|
| Copolymer only | 0 | Soft clayey substance which easily deforms by finger pressure, shows tackiness which increases by softening and changing to a starch syrup-like state when heated (55° C.), | 0 | 1.0 |
| d | 25 | Paper clay-like substance, hardens due to mixing of CM chitin, tackiness does not change but increases by softening when heated (55° C.) | 24 | 2.1 |
| e | 50 | Paper clay-like substance which hardens and loses tackiness due to mixing of large amount of CM chitin, tackiness is increased by softening when heated (55° C.). | 69 | 3.0 |

As is evident from Table 7, swelling ability by water can be added to the adhesive substance when mixing with CM chitin. Because of this, when a bone growth factor such as BMP (bone morphogenic protein) is added to the adhesive substance at the time of its packing into a bone defect for example, it swells in the bone hole and contacts with the bone wall so that formation and replacement of bone can be made efficiently.

EXAMPLE 8

The p-DOX/D,L-lactic acid copolymer having a weight average molecular weight of 28,100 obtained in Example 6 was kneaded with 25 or 50% by weight of poly-p-dioxanone (weight average molecular weight 18,600, melting point 110.7° C.) and heated at 115° C. to obtain mixtures f and g.

Properties and Shore hardness at 37° C. of the copolymer and its mixtures f and g are shown in Table 8.

TABLE 8

| Mixture | Mixing ratio of p-DOX (wt %) | Properties | Hardness (37° C.) |
|---|---|---|---|
| Copolymer only | 0 | Soft clayey substance which easily deforms by finger pressure, shows tackiness which increases by softening and changing to a starch syrup-like state when heated (55° C.) | 0 |
| f | 25 | Waxy substance hardens due to mixing of p-DOX, almost no tackiness, tackiness increases by softening when heated (55° C). | 40 |
| g | 50 | Waxy substance hardens and loses tackiness due to mixing of large amount of p-DOX, tackiness is generated by softening when heated (55° C.). | 68 |

EXAMPLE 9

The p-DOX/D,L-lactic acid copolymer (No. 7) having a weight average molecular weight of 21,200 obtained in Example 2 was selected and heated at about 50° C. By this treatment, the copolymer expressed unrestricted plastic deformation ability so that it was able to form it into optional and complex three-dimensional shapes.

EXAMPLE 10 p-DOX and D,L-lactic acid were allowed to undergo at a mixing molar ratio of 1:1, 2:1 or 3:1, thereby obtaining a p-DOX/D,L-lactic acid copolymer having a weight average molecular weight of 31,000, 24,000 or 20,000, respectively.

Each of these copolymers was soaked in 0.2 M phosphate buffer (pH 7.4) at 37° C., taken out after a predetermined period of time and then dried. Then, its weight average molecular weight was measured by GPC (gel permeation chromatography). Weight average molecular weight of each copolymer was reduced to about 5,000 after 4 weeks of the soaking, and to about 1,000 after 10 to 12 weeks, by hydrolysis. A slight difference in the initial molecular weight did not apparently influence on the average molecular weight after degradation.

Decrease with the passage of time in the molecular weight of the copolymer having a mixing molar ratio of 1:1 caused by hydrolysis is shown in FIG. 1. It is considered that this copolymer is completely degraded and disappeared after about 3 to 4 months, though it may vary depending on its amount and the region to be Implanted in vivo.

EXAMPLE 11

A p-DOX/D,L-lactic acid copolymer having a p-DOX/D, L-lactic acid molar ratio of 1:1 and a weight average molecular weight of 21,000 was softened by heating it at 50 to 60° C. and then mixed and kneaded with 10% by weight of an anticancer agent adriamycin (ADM). This was soaked in 0.2 M phosphate buffer (pH 7.4) at 37° C., and released amount of the drug caused by degradation of the copolymer was measured after a predetermined period of time.

Figure 2:
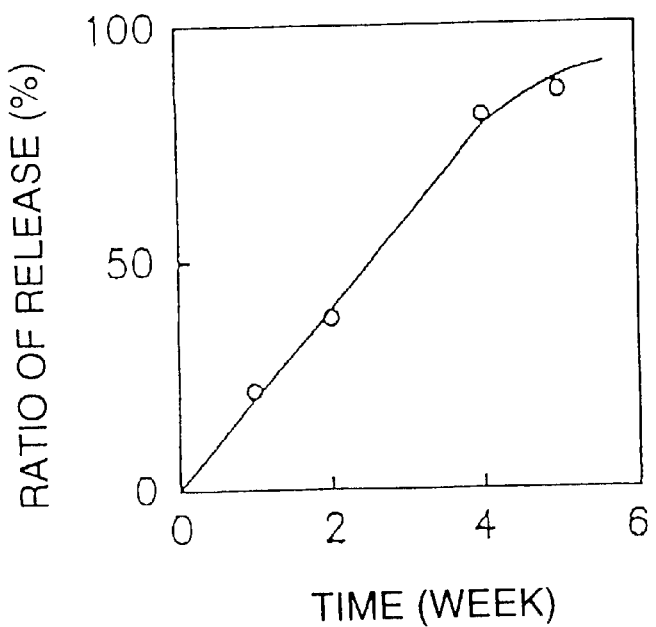
FIG. 2 is a graph showing periodical changes in the amount of released drug by hydrolysis when a p-DOX/D, L-lactide copolymer according to an example of the present invention is kneaded with a drug (ADR) and soaked in PBS at 37° C.

As the results, constant release of the drug was found as shown in FIG. 2, and it was confirmed that 80% of ADM initially mixed was released after 4 weeks. On the basis of these results, it was revealed that this copolymer is excellent as a carrier of DDS.

Thus, as is evident from the aforementioned descriptions, within the range of from the skin temperature to the body temperature (approximately from 30 to 40° C.), the biodegradable polymeric clayey and sticky substance or clayey substance of the present invention is a putty-, paste- or gum-like substance which has appropriate tackiness (pressure sensitive adhesion) but is not a solid (powder) or waxy substance, so that it is not too sticky and has unrestricted deforming plasticity but is not easily deformed by its own weight by becoming fluid liquid, or, at a temperature equal to or higher than the body temperature (37 to 40° C.), it also shows such properties that it can adhered to regions to be adhered by fluidizing and hot-melting into paste-, syrup- or jelly-like form, and it is degraded and absorbed in, and excreted from, the living body at a relatively early stage.

In addition, it is not always necessary to carry out its mixing with drugs, bioceramics powder and other additives at the time of its production, because it can be made at the time of surgical operation by optionally adjusting the mixing ratio and shape at will taking into consideration morbid state, size of the damaged region and conditions of each patient, so that this is a markedly convenient and practical material having excellent biocompatibility.

In consequence, making use of these many superior properties, the clayey and sticky substance of the present invention can be used suitably as, for example, a hemostatic material, an adhesive material for tissues, a prosthetic material or scaffold for tissue reconstruction use, a carrier of drug delivery system, a plugging material, a filler and an accretion-preventing material, as such or by mixing with drugs and other additives.

While the invention has been described in detail and with reference to specific embodiments thereof, it will be apparent to one skilled in the art that various changes and modifications can be made therein without departing from the spirit and scope thereof.

What is claimed is:

1. A bioresorbable polymeric clayey and sticky substance which comprises at least one copolymer selected from the group consisting of a copolymer of p-dioxanone with D-lactide, which has a weight average molecular weight of from 2,000 to 40,000, a copolymer of p-dioxanone with L-lactide, which has a weight average molecular weight of from 2,000 to 40,000 and a copolymer of p-dioxanone with D, L-lactide, which has a weight average molecular weight of from 3,000 to 50,000, wherein the ratio of p-dioxanone occupying the copolymer is from 50 to 95 mol %, and wherein said substance shows tackiness, plasticity and shape holding ability at a temperature of approximately from 30 to 40° C. and can increase its fluidity to give an optional shape at 40° C. or higher.

2. A bioresorbable polymeric clayey and sticky substance comprising a star-shaped copolymer comprised of a core of a multifunctional alcohol and one of the copolymers as defined in claim 1 as segment chains substituted on the multifunctional alcohol.

3. The bioresorbable polymeric clayey and sticky substance according to claim 2, wherein said multifunctional alcohol is at least one member selected from the group consisting of glycerol, polyglycerol, and pentaerythritol.

4. The bioresorbable polymeric clayey and sticky substance according to claim 1, wherein adhesion of the copolymer measured at 37° C. by the 90° peeling test of JIS Z 0237-1991 is from 30 to 1,500 g (½ inch in width).

5. The bioresorbable polymeric clayey and sticky substance according to claim 1, which further comprises a poly-p-dioxanone having a weight average molecular weight which is larger than that of said copolymer.

6. The bioresorbable polymeric clayey and sticky substance according to claim 1, which has bubbles.

7. A hemostatic material, which comprises any one of the bioresorbable polymeric clayey and sticky substances of claims 1–6 and which further comprises at least one member selected from the group consisting of blood coagulation factors, drugs, cellulose oxide fibers, gelatin sponge and micro-fibrous collagen.

8. An adhesive material or clayey material for tissues, which comprises any one of the bioresorbable polymeric clayey and sticky substances of claims 1–6 and which further comprises at least one member selected from the group consisting of active ceramics powder, cytokine, derivatives of chitin or chitosan, hyaluronic acid, drugs, and other bioresorbable polymers.

9. The adhesive material according to claim 8, wherein the adhesion of said material measured at 37° C. by the 90° peeling test of JIS Z 0237-1991 is from 100 to 1,300 g (½ inch in width).

10. A prosthetic material for tissue reconstruction use, which comprises any one of the bioresorbable polymeric clayey and sticky substances of claims 1–6 and which further comprises at least one member selected from the group consisting of bioactive ceramics powder, cytokine, derivatives of chitin or chitosan, hyaluronic acid, drugs, bone fragments, cartilage fragments, and other bioresorbable polymers.

11. A carrier for drug delivery system use, which comprises any one of the bioresorbable polymeric clayey and sticky substances of claims 1–6 and which further comprises at least one member selected from the group consisting of synthetic or natural drugs, hormones, cytokine and enzymes.

12. A bioresorbable polymeric clayey and sticky substance which comprises at least one copolymer selected from the group consisting of a copolymer of p-dioxanone with D-lactide, which has a weight average molecular weight of from 2,000 to 40,000, a copolymer of dioxanone with L-lactide, which has a weight average molecular weight from 2,000 to 40,000 and a copolymer of p-dioxanone with D,L-lactide, which has a weight average molecular weight of from 3,000 to 50,000, wherein the ratio of p-dioxanone occupying the copolymer is from 50 to 95 mol %, and wherein said substance has not or slight tackiness at a temperature of lower then 30° C., but has tackiness, plasticity and shape holding ability at a temperature of approximately from 30 to 40° C. and can increase its fluidity to give an optional shape at 40° C. or higher.

\* \* \* \* \*